United States Patent
Blumenzweig et al.

(10) Patent No.: US 9,526,404 B2
(45) Date of Patent: Dec. 27, 2016

(54) ENDOSCOPE ILLUMINATION SYSTEM

(71) Applicant: GYRUS ACMI INC., Southborough, MA (US)

(72) Inventors: Arie Blumenzweig, Netanya (IL); Stuart Wolf, Yokneam (IL); Igor Kagan, Kiryat Biyalik (IL)

(73) Assignee: GYRUS ACMI, INC., Southborough, MA (US)

( * ) Notice: Subject to any disclaimer, the term of this patent is extended or adjusted under 35 U.S.C. 154(b) by 379 days.

(21) Appl. No.: 14/046,975

(22) Filed: Oct. 6, 2013

(65) Prior Publication Data
US 2015/0099929 A1 Apr. 9, 2015

(51) Int. Cl.
*A61B 1/06* (2006.01)
*A61B 1/00* (2006.01)
*A61B 1/045* (2006.01)

(52) U.S. Cl.
CPC ........... *A61B 1/00114* (2013.01); *A61B 1/045* (2013.01); *A61B 1/0669* (2013.01); *A61B 1/0684* (2013.01)

(58) Field of Classification Search
CPC ... A61B 1/045; A61B 1/00006; A61B 5/0059; A61B 1/00066; A61B 1/00052; A61B 1/00105; A61B 1/0052; A61B 1/05; A61B 1/051; A61B 1/0669; A61B 1/0676; A61B 1/0684; A61B 1/07
USPC ........ 600/109, 118, 131, 134, 160, 178, 180
See application file for complete search history.

(56) References Cited

U.S. PATENT DOCUMENTS

| 6,181,077 B1 * | 1/2001 | Greenland | ......... | H05B 41/2925 315/224 |
| 6,416,509 B1 * | 7/2002 | Goble | .................. | A61B 18/082 606/37 |
| 6,963,175 B2 * | 11/2005 | Archenhold | ....... | H05B 33/0818 315/246 |

(Continued)

FOREIGN PATENT DOCUMENTS

JP  2013062032 A   4/2013
WO  2012165172 A1  12/2012

OTHER PUBLICATIONS

International Application # PCT/US14/58500 Search Report dated Apr. 8, 2015.

(Continued)

*Primary Examiner* — John P Leubecker
*Assistant Examiner* — Arnaldo Torres Diaz
(74) *Attorney, Agent, or Firm* — D. Kligler I.P. Services Ltd.

(57) ABSTRACT

Imaging apparatus, including an imaging unit, which consists of an image sensor, configured to capture images of a region and to output image signals in response to the captured images and an illumination source, configured to illuminate the region. The unit further includes a driver circuit, which is coupled to receive a digital value indicative of a target luminous flux of the illumination source and to generate a pulse-width-modulated (PWM) signal to drive the illumination source with a duty cycle of the signal determined by the value. The apparatus includes a camera control unit, which is configured to process the image signals so as to generate images of the region and to output the digital value indicative of the target luminous flux based on the images. A single cable connects the imaging unit to the camera control unit so as to convey the image signals and the digital value.

6 Claims, 3 Drawing Sheets

(56) References Cited

U.S. PATENT DOCUMENTS

| | | | |
|---|---|---|---|
| 7,232,410 B2* | 6/2007 | Takahashi | A61B 1/0638 348/69 |
| 7,410,462 B2 | 8/2008 | Navok et al. | |
| 7,504,780 B2* | 3/2009 | Isobe | H04N 9/3114 315/194 |
| 7,772,786 B2* | 8/2010 | Hosoda | A61B 1/00034 315/291 |
| 8,110,999 B2* | 2/2012 | Ikeda | A61B 1/0669 315/246 |
| 8,785,833 B2* | 7/2014 | Yabe | G02B 23/2469 250/208.1 |
| 9,107,578 B2* | 8/2015 | Ziberstein | A61B 1/06 |
| 9,155,457 B2* | 10/2015 | Yamashita | A61B 1/0638 |
| 2001/0028227 A1* | 10/2001 | Lys | A61N 5/0616 315/317 |
| 2003/0193314 A1* | 10/2003 | Solingen | A61B 5/0059 320/107 |
| 2004/0122291 A1* | 6/2004 | Takahashi | A61B 1/0638 600/180 |
| 2004/0171915 A1* | 9/2004 | Glukhovsky | A61B 1/041 600/160 |
| 2005/0099824 A1* | 5/2005 | Dowling | A61B 1/0653 362/572 |
| 2007/0167681 A1* | 7/2007 | Gill | A61B 1/00059 600/112 |
| 2008/0027280 A1* | 1/2008 | Fengler | A61B 1/00096 600/112 |
| 2008/0180953 A1* | 7/2008 | Isobe | H04N 9/3114 362/293 |
| 2009/0062617 A1* | 3/2009 | Mizuyoshi | A61B 1/0638 600/178 |
| 2009/0076329 A1 | 3/2009 | Su et al. | |
| 2009/0187077 A1* | 7/2009 | Hosoda | A61B 1/0669 600/178 |
| 2010/0277087 A1* | 11/2010 | Ikeda | A61B 1/0669 315/250 |
| 2011/0018988 A1* | 1/2011 | Kazakevich | A61B 1/00016 348/68 |
| 2011/0112361 A1 | 5/2011 | Ishigami et al. | |
| 2011/0174861 A1 | 7/2011 | Shelton et al. | |
| 2011/0301412 A1* | 12/2011 | Cho | A61B 1/00091 600/104 |
| 2012/0116157 A1* | 5/2012 | Seto | A61B 1/00057 600/109 |
| 2012/0123213 A1* | 5/2012 | Seto | A61B 1/0638 600/178 |
| 2013/0193875 A1* | 8/2013 | Godo | A61B 1/0684 315/297 |
| 2014/0014820 A1* | 1/2014 | Yabe | G02B 23/2469 250/208.1 |
| 2014/0203711 A1* | 7/2014 | Saccomanno | G09G 3/3406 315/151 |
| 2014/0293038 A1* | 10/2014 | Delmonico | H04N 5/2256 348/82 |

OTHER PUBLICATIONS

International Application # PCT/US14/58500 Search Report dated Feb. 2, 2015.

* cited by examiner

ENDOSCOPE ILLUMINATION SYSTEM

FIELD OF THE INVENTION

The present invention relates generally to operation of an endoscope, and specifically to an illumination system used for the endoscope.

BACKGROUND OF THE INVENTION

An endoscope typically images a body cavity, and in order to image the cavity the cavity must be illuminated.

U. S. Patent Application 2009/0076329 to Su et al., whose disclosure is incorporated herein by reference, describes a disposable stereoscopic endoscope which has two imaging sensors and a solid state illumination source arranged inside the endoscope.

U. S. Patent Application 2011/0174861 to Shelton et al., whose disclosure is incorporated herein by reference, describes a surgical instrument with wireless communication between a control unit and a remote sensor. The disclosure states that the instrument may include a display powered by a battery and controlled by the control unit.

U.S. Pat. No. 7,410,462 to Navok et al., whose disclosure is incorporated herein by reference, describes a hermetic endoscope assemblage having compound optical widows. The disclosure states that the compound optical windows may have separate panes for an imaging system and an illumination system.

A "DUR-D" ureteroscope, produced by Olympus Corporation, of Tokyo, Japan, uses an endoscope protection system which exploits the ability of a CMOS sensor incorporated into the ureteroscope to detect colors. Information transmitted from the CMOS sensor to a control unit of the ureteroscope is used to quickly shut down a laser of the ureteroscope.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides imaging apparatus, including:

an imaging unit, which consists of:

an image sensor, configured to capture images of a region and to output image signals in response to the captured images;

an illumination source, configured to illuminate the region; and a driver circuit, which is coupled to receive a digital value indicative of a target luminous flux of the illumination source and to generate a pulse-width-modulated (PWM) signal to drive the illumination source with a duty cycle of the signal determined by the value;

a camera control unit, which is configured to process the image signals so as to generate images of the region and to output the digital value indicative of the target luminous flux based on the images; and a single cable connecting the imaging unit to the camera control unit so as to convey the image signals and the digital value.

Typically, the illumination source includes a light emitting diode (LED). A current provided by the driver circuit in an on-state of the duty cycle may be a minimum operating current of the LED.

A disclosed embodiment further includes a direct (DC) current source configured to drive the illumination source, wherein below a bounding value of the target luminous flux the driver circuit generates the PWM signal, and above the bounding value the DC source generates a DC current according to the target luminous flux. Typically, the driver circuit is located within a handle of an endoscope, and the DC source is located within the camera control unit. The driver circuit may be implemented as a variable current load.

In a further disclosed embodiment the single cable is configured to convey direct (DC) current from the camera control unit to the driver circuit so as to power the driver circuit.

In a yet further disclosed embodiment the imaging unit is included within an endoscope, and the illumination source and the driver circuit are located within a handle of the endoscope, and the handle is configured to be held by an operator of the endoscope for manipulation thereof.

There is further provided, according to an embodiment of the present invention, apparatus, including:

an endoscope, including:

a tube having a proximal end and a distal end configured for insertion into a body cavity;

an image sensor, mounted at the distal end and configured to generate image signals of a region of the body cavity in response to illumination received therefrom;

a handle, configured to fixedly connect to the proximal end of the tube and configured to be held by an operator of the endoscope for manipulation thereof;

a driver circuit mounted within the handle, configured to generate pulse-width-modulated (PWM) current; and an illumination source, mounted within the handle, configured to receive the PWM current and in response to illuminate the body cavity so as to provide the illumination received therefrom; and a camera control unit (CCU), configured to control the image sensor and to generate an image of the body cavity in response to receipt of the image signals.

In an alternative embodiment the driver circuit is powered by a direct (DC) current, the apparatus further including a single cable connected between the CCU and the handle and configured to transfer the DC current to the driver circuit and to transfer the image signals to the CCU.

Typically, the PWM current is supplied by the driver circuit to the LED at a duty cycle, and a current provided by the driver circuit in an on-state of the duty cycle is a minimum operating current of the LED.

The CCU may be configured to process the image signals so as to output a digital value indicative of a target luminous flux of the illumination source, and the driver circuit may be coupled to receive the digital value and to generate the PWM current with a duty cycle determined by the value.

The apparatus may include a direct (DC) current source configured to drive the illumination source, so that below a bounding value of the target luminous flux the driver circuit generates the PWM signal, and above the bounding value the DC source generates a DC current according to the target luminous flux.

The apparatus may include a single cable, connecting the endoscope to the CCU, that is configured to convey the image signals from the image sensor to the CCU, and to convey direct (DC) current from the CCU to the driver circuit so as to power the driver circuit.

There is further provided, according to an embodiment of the present invention, a method for imaging, including:

configuring an image sensor within an imaging unit to capture images of a region and to output image signals in response to the captured images;

configuring an illumination source within the imaging unit to illuminate the region;

configuring a driver circuit within the imaging unit to receive a digital value indicative of a target luminous flux of the illumination source and to generate a pulse-width-modulated (PWM) signal to drive the illumination source with a duty cycle of the signal determined by the value;

processing the image signals in a camera control unit so as to generate images of the region and to output the digital value indicative of the target luminous flux based on the images; and connecting the imaging unit to the camera control unit with a single cable so as to convey the image signals and the digital value.

There is further provided, according to an embodiment of the present invention, a method including:

inserting a tube of an endoscope into a body cavity, the tube having a proximal end and a distal end;

mounting an image sensor of the endoscope at the distal end and generating with the image sensor image signals of a region of the body cavity in response to illumination received therefrom;

fixedly connecting a handle of the endoscope to the proximal end of the tube, the handle being configured to be held by an operator of the endoscope for manipulation thereof;

mounting a driver circuit within the handle, and generating pulse-width-modulated (PWM) current with the driver circuit;

mounting an illumination source within the handle, and configuring the source to receive the PWM current and in response to illuminate the body cavity so as to provide the illumination received therefrom; and configuring a camera control unit (CCU) to control the image sensor and to generate an image of the body cavity in response to receipt of the image signals.

The present invention will be more fully understood from the following detailed description of the embodiments thereof, taken together with the drawings in which:

DETAILED DESCRIPTION OF EMBODIMENTS

Overview

An embodiment of the present invention comprises an endoscope which is connected by a single cable to a camera control unit (CCU), the CCU operating the endoscope. An image sensor in the endoscope generates image signals of an image captured by the endoscope, and the image signals are transferred via the single cable to the CCU, which processes the signals to display a corresponding image on a screen connected to the CCU. In a handle of the endoscope an illumination source, typically a light emitting diode (LED) is mounted, and the illumination source is driven by a driver circuit which is also mounted within the handle. Illumination provided by the source generates the image captured by the image sensor.

Continuous direct (DC) current or pulse-width-modulated (PWM) current may be supplied to the illumination source, which correspondingly generates continuous or pulsed luminous flux. Typically, a driver circuit is configured to supply the PWM current at different duty cycles when the illumination source is required to generate low average flux levels, the duty cycle being adjusted according to a required low flux level. In addition, a DC source, typically mounted in the CCU, may be configured to supply continuous DC current at a level that is adjusted according to a required high flux level.

Typically, the CCU is configured to calculate a digital value according to a target luminous flux required from the illumination source. The digital value may set if PWM or continuous DC current is to be generated, and may also set the duty cycle (for the PWM).

By locating the driver circuit in the handle of the endoscope, embodiments of the present invention only generate PWM current within the handle. Thus, in the single cable connecting the CCU to the endoscope, there is no transfer of PWM current. (In prior art systems this type of transfer causes interference in the image signals transferred in the cable.) Rather, in embodiments of the present invention, even when PWM current is required from the driver circuit, only the DC current needed to power the driver circuit is transferred via the single cable, so that there is no interference with the image signals in the cable.

DETAILED DESCRIPTION

Figure 1:
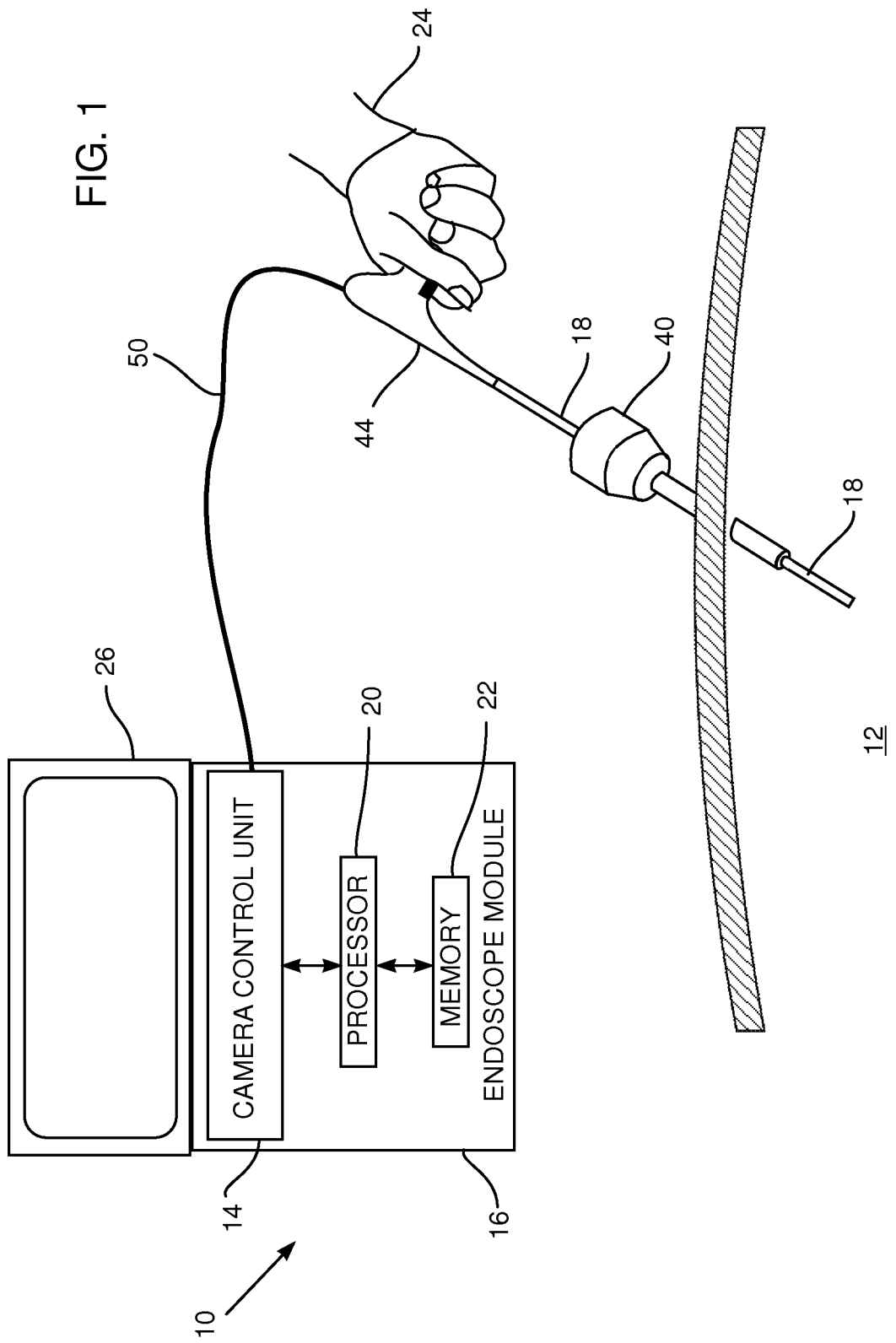
FIG. 1 is a schematic illustration of an endoscope illumination system, according to an embodiment of the present invention.

Reference is now made to FIG. 1, which is a schematic illustration of an endoscope illumination system 10, according to an embodiment of the present invention. System 10 may be used in an invasive medical procedure, typically a minimally invasive procedure, on a body cavity 12 of a patient in order to image a region of the body cavity. By way of example, in the present description the body cavity is assumed to be the abdomen of a patient, and body cavity 12 is also referred to herein as abdomen 12. However, it will be understood that system 10 may be used to image a region in substantially any body cavity, such as the bladder or the chest, or in another entity.

System 10 is operated by a camera control unit (CCU) module 14, located in an endoscope module 16 which operates an endoscope 18. Endoscope module 16 comprises a processor 20 communicating with a memory 22, and the processor and memory may be used by the endoscope module in order to control CCU module 14, as well as to perform at least some of the functions of the CCU module, described below.

Endoscope module 16 may also comprise other modules, such as an image processing module and a zoom/pan module, which may be used by processor 20, but which for simplicity are not shown in the diagram. The processor uses software stored in memory 22, in the form of the modules referred to above as well as in other forms, to operate system 10. Results of the operations performed by processor 20 may be presented on a screen 26 to an operator 24, assumed by way of example to be a medical physician, of system 10. Screen 26 typically displays an image, acquired by endoscope 18, of a region of body cavity undergoing the procedure. Alternatively or additionally, screen 26 may be used to display a graphic user interface to operator 24. The software may be downloaded to processor 20 in electronic form, over a network, for example, or it may, alternatively or additionally, be provided and/or stored on non-transitory tangible media, such as magnetic, optical, or electronic memory.

To perform a procedure, the physician inserts a trocar 40 into abdomen 12, and then inserts endoscope 18 into the abdomen via the trocar. So that the physician can manipulate the endoscope, the endoscope is attached to a handle 44 which is configured to be gripped by the physician. Typically, handle 44 and endoscope 18 are produced as a single unitary system wherein the handle and the endoscope are fixedly attached.

Elements of endoscope 18 are controlled by CCU module 14, and in order to provide this control handle 44 is connected by a single cable 50 to the CCU module. The elements of endoscope 18 that are controlled by the CCU module are described in more detail with reference to FIG. 2 below.

Figure 2:
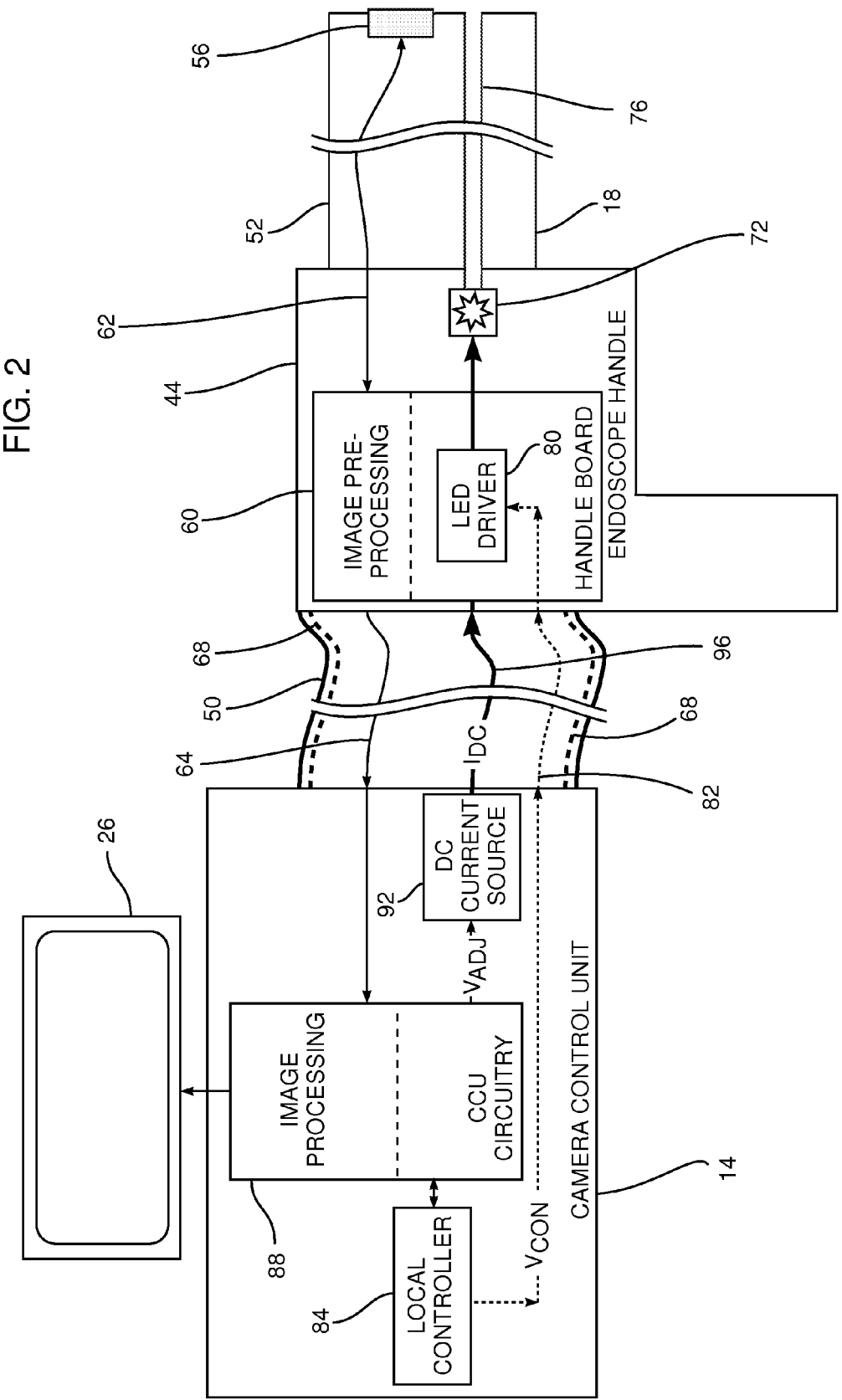
FIG. 2 is a schematic diagram illustrating elements of an endoscope, a handle, and a camera control unit module, according to an embodiment of the present invention.

FIG. 2 is a schematic diagram illustrating elements of endoscope 18, handle 44, and CCU module 14, according to an embodiment of the present invention. Endoscope 18 comprises a tube 52 which may be rigid or flexible. The tube is connected at its proximal end to handle 44. An image sensor 56, located at the distal end of tube 52, is arranged to capture images of a region of cavity 12. For its operation, the image sensor receives driving signals, generated by sensor circuitry 60 which acts as a sensor driver. Circuitry 60 is located within handle 44, is typically implemented as a printed circuit board, and is also referred to herein as handle board 60. In operation, sensor 56 generates image signals corresponding to the captured images, and transfers the image signals to handle board 60 wherein the image signals are pre-processed. The driving signals and the image signals are typically transferred between handle board 60 and sensor 56 using a cable 62, which traverses tube 52.

The pre-processing performed by board 60 converts the image signals into conditioned signals, which are in a form suitable for transmission to CCU module 14 via a conductor 64 in cable 50. Cable 50 comprises other conductors, the functions of which are described below, and the conductors within the cable are typically shielded by a cable shield 68 which may be configured to act as a return. Typically, the pre-processing performed by board 60 to generate conditioned signals comprises amplification, filtration, and impedance conversion of the image signals.

The region of cavity 12 that is imaged by sensor 56 is illuminated from an illumination source 72, which comprises a light emitting diode (LED), so that source 72 is also referred to herein as LED 72. Typically LED 72 is mounted in handle 44, and the illumination generated by the LED may be transferred from the LED, so that it exits from the distal end of tube 52, by a fiber optic 76. LED 72 may be driven by a LED driver circuit 80, which is incorporated within handle 44, typically by being configured as part of handle board 60. Driver circuit 80 provides pulse width modulated (PWM) driving current to LED 72 according to a digital value $V_{CON}$ received, typically as a communication signal, by the circuit, and the manner of operation of the driver circuit is described below. Alternatively, LED 72 may be driven with DC current by a DC current source block 92 in CCU module 14. DC current source 92 is also described below.

Figure 3:
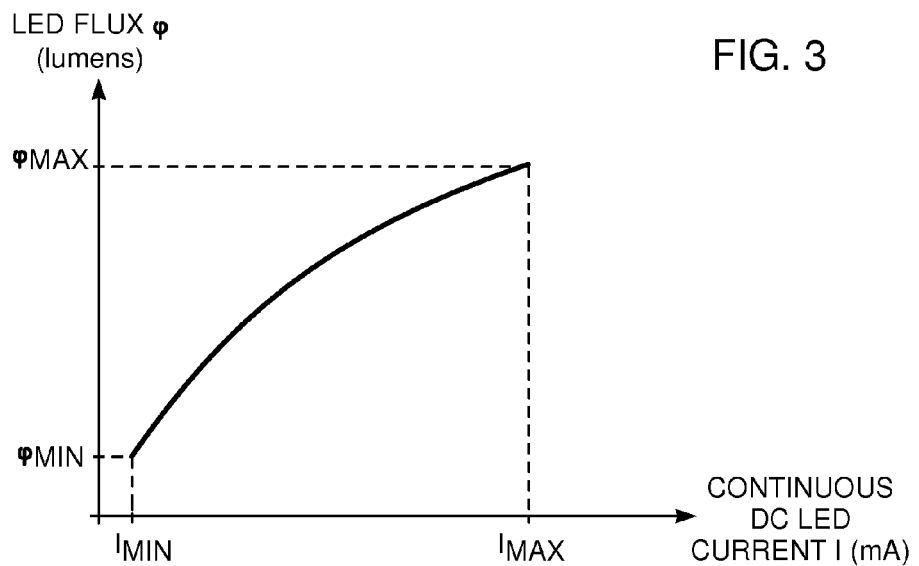
FIG. 3 is a schematic graph of luminous flux emitted by a light emitting diode (LED) vs. current driving the LED, according to an embodiment of the present invention.

FIG. 3 is a schematic graph of luminous flux emitted by LED 72 vs. current driving the LED, according to an embodiment of the present invention. The flux $\phi$ is measured in lumens, and the current I is continuous direct (DC) current measured in mA. The graph illustrates that as the current increases, the flux emitted by LED 72 also increases. Since the DC current is continuous, the flux emitted by the LED is also continuous. The graph also illustrates that there is a minimum DC current $I_{MIN}$, at which the flux emitted by the LED is a minimum flux $\phi_{MIN}$. Typically, a specification for the LED does not include operating currents below $I_{MIN}$, since for such currents the quality of the flux emitted by the LED is uncertain. Consequently, for stable operation within its specification, the LED is not operated at currents below $I_{MIN}$, so that the graph has a first termination at this current. The graph has a second termination at a maximum current $I_{MAX}$ at which the LED is able to operate. At the maximum current, LED 72 emits a maximum flux $\phi_{MAX}$.

In order for LED 72 to emit an average luminous flux less than $\phi_{MIN}$, embodiments of the present invention pulse the LED intermittently between an on-state and an off-state, using pulse-width-modulation (PWM). In the on-state the LED is driven with a DC current $I_{MIN}$ or higher; in the off-state there is no driving current for the LED.

For LED 72 to emit flux at levels above and below the minimum flux level $\phi_{MIN}$ the LED is configured to operate in one of two states:

In a continuous operating state the LED receives a continuous DC current, with a value greater than or equal to $I_{MIN}$.

In a PWM operating state the LED receives a pulsed DC current, with a duty cycle that may be varied, but so that in the on-state of the LED the current supplied to the LED is greater than or equal to $I_{MIN}$.

The two different operating states of LED 72 are described in more detail below.

In the continuous operating state of the LED, the flux emitted by LED 72 is according to the continuous DC current driving the LED. In this state the current driving the LED is greater than or equal to $I_{MIN}$, and in response the flux emitted by the LED is continuous and is greater than or equal to $\phi_{MIN}$.

In the PWM operating state of the LED, the flux emitted by LED 72 depends on the duty cycle of the pulsed DC current driving the LED, and is also dependent on the level of the pulsed DC current in the duty cycle on-state. (As stated above, the level of the DC current in the on-state is greater than or equal to $I_{MIN}$.) For example, if the current in the on-state is equal to $I_{MIN}$, then the flux emitted from the LED can be varied between 0 lumens, for a duty cycle of 0, and $\phi_{MIN}$ lumens, for a duty cycle of 100%.

Returning to FIG. 2, CCU module 14 comprises a local controller 84, CCU circuitry 88, and a DC current source block 92. Circuitry 88 includes an image processing section which receives the pre-processed image signals from board 60, and in response generates final image signals of an image to be displayed on screen 26. Typically, CCU 14 receives image data from an image pre-processing section of board 60, and uses the data, in an automatic light control (ALC) system, to drive LED so that images presented on screen 26 are within an acceptable dynamic range of brightness, i.e., have neither completely saturated nor completely unsaturated portions. Circuitry 88, under control of local controller 84, implements the ALC system to adjust the received pre-processed signals, whose effective brightness is a function of the illumination flux transmitted by the LED into cavity 12, and to achieve final image signals having the brightness set by operator 24. Typically, circuitry 88 is implemented as a field programmable gate array (FPGA).

The effective brightness of the pre-processed signals is a function of the flux emitted by the LED, and in turn the flux is a function of the mean DC current supplied to the LED. Controller 84 is coupled to circuitry 88, and uses the coupling to decide on a mean target luminous flux, $\phi_T$, to be emitted by the LED. From the mean target luminous flux the controller calculates a desired mean DC current to be supplied to the LED. If the desired mean DC current is below $I_{MIN}$, the controller transmits a digital control signal $V_{CON}$, corresponding to the desired mean target luminous flux and the desired mean DC current, to driver 80 via a conductor 82 in cable 50. In the description herein, control signal $V_{CON}$ is assumed, by way of example and for simplicity, to be positive.

Figure 4:
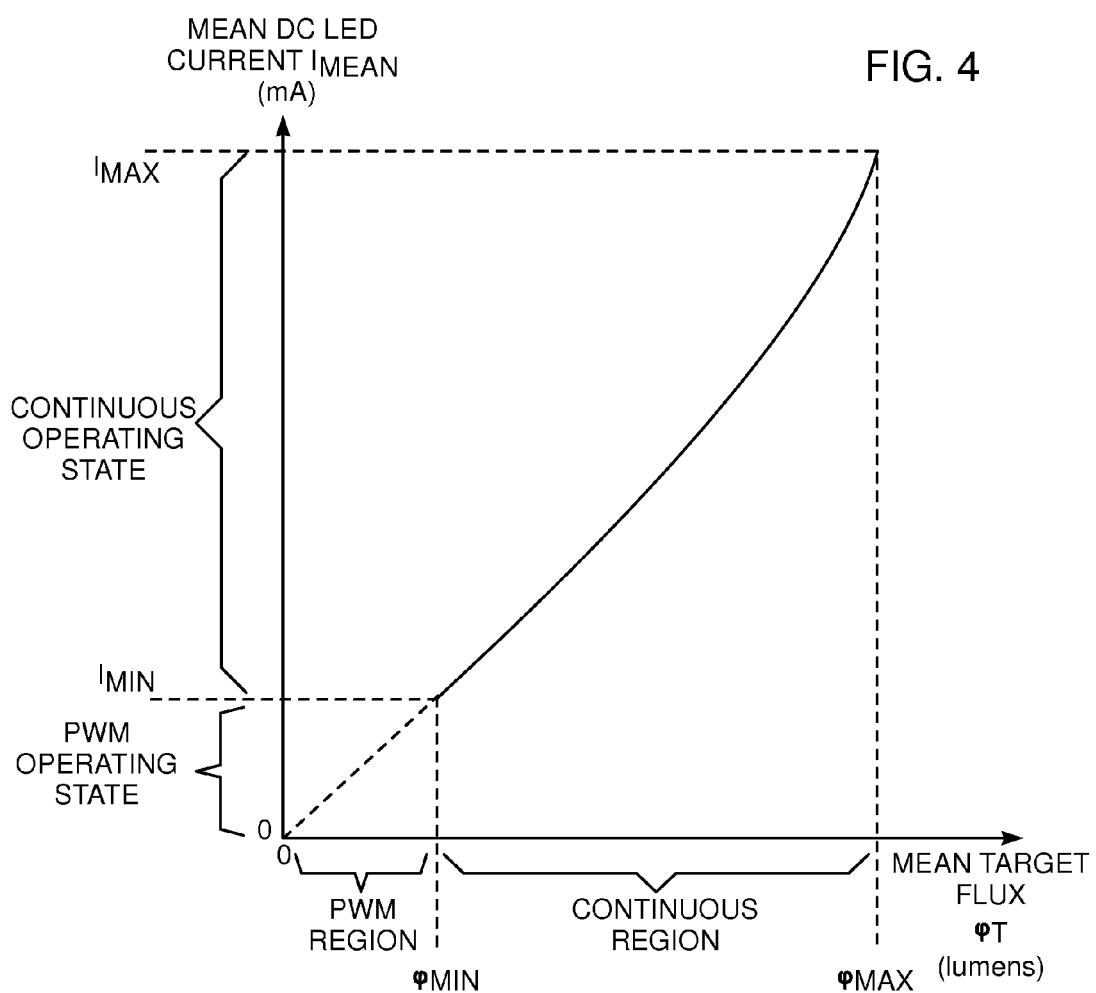
FIG. 4 is a schematic graph of mean DC current drawn by a LED vs. mean target flux of the LED, according to an embodiment of the present invention.

FIG. 4 is a schematic graph of mean DC current, $I_{MEAN}$, drawn by LED 72 vs. mean target flux $\phi_T$ of the LED, according to an embodiment of the present invention. The graph illustrates two regions of operation of LED 72:

A PWM region, defined by the range of values of the mean target flux $\phi_T$ given by expression (1):

$$0 \le \phi_T < \phi_{MIN} \quad (1)$$

In the PWM region LED 72 operates in a pulsed flux transmitting state, by driver 80 operating in the PWM operating state referred to above. In this state the driver supplies pulsed DC, also termed PWM, current to the LED. The duty cycle of the pulses supplied in the PWM state typically varies between 0 and 100%. The DC current in the on-state of the duty cycle is typically $I_{MIN}$, although the DC current in the on-state may be higher than $I_{MIN}$. For simplicity, in the following description the DC current drawn by the LED in its on-state is assumed to be $I_{MIN}$. (Those having ordinary skill in the art will be able to adapt the description, mutatis mutandis, for cases where the DC current in the on-state of the PWM duty cycle is higher than $I_{MIN}$, in which case the maximum duty cycle value may be less than 100%.) The mean DC current of the LED in the PWM operating state of its driver is in the range given by expression (2):

$$0 \le I < I_{MIN} \quad (2)$$

It will be understood from the above that in the PWM region, corresponding to the operating state of driver 80, the flux is pulsed, and the value of the mean flux $\phi_T$ is dependent on the duty cycle of the pulses supplied by the driver.

A continuous region of operation of LED 72 is defined by the range of values of the mean target flux $\phi_T$ given by expression (3):

$$\phi_{MIN} \le \phi_T \le \phi_{MAX} \quad (3)$$

In the continuous region LED 72 operates in a continuous transmitting state, where current source 92 supplies a constant DC current to the LED. The supplied DC current is given by expression (4):

$$I_{MIN} \le I \le I_{MAX} \quad (4)$$

From consideration of the above expressions and of the description associated with the expressions, it will be understood that the minimum flux level $\phi_{MIN}$ acts as a bounding value: for a mean target flux $\phi_T$ below $\phi_{MIN}$ LED 72 operates in a PWM state; above $\phi_{MIN}$ the LED operates in a continuous state.

Returning to FIG. 2, controller 84 uses circuitry 88 to assess a current demand for LED 72. If the demand is within the range given by equation (4), then circuitry 88 outputs a signal $V_{ADJ}$, having a value dependent on the current demand, to DC current source 92. On receipt of $V_{ADJ}$, source 92 generates an appropriate current, $I_{DC}$, which is supplied directly to LED 72.

If the current demand for LED 72 is within the range given by equation (2), then instead of LED 72 being driven by source 92, the LED is driven, in a PWM mode, by driver 80. In this case, controller 84 outputs a signal $V_{CON}$, having a value dependent on the mean current demand of the LED, to driver 80, and the driver supplies an appropriate PWM current to the LED.

In an alternative embodiment, driver 80 is implemented as a variable current load. While the current demand for LED 72 is in the range given by equation (4), then driver 80 is configured as a zero load, and $I_{DC}$ is supplied to the LED. If the current demand for the LED is in the range given by equation (2), then driver 80 is configured to vary its load characteristics in a switching manner, so as to generate the appropriate PWM current and to supply this PWM current to the LED.

In all cases no PWM current is conveyed through cable 50. Rather, for the purpose of driving LED driver 80, only DC current is conveyed through the cable.

As is described above, cable 50 comprises conductors 64, 96, and 82 which respectively transfer digital image signals, DC current, and a digital control value. The pulse-width-modulated current used by LED 72 is produced by LED driver 80. By locating driver 80 in handle 44 there is no need for any pulse-width-modulated current to be transferred via cable 50. Thus, unlike prior art systems wherein pulse-width-modulated current for powering an LED is transferred in the same cable as digital image signals, causing interference with the image signals, in embodiments of the present invention no pulse-width-modulated current is transferred in cable 50. Rather, the power needed for the pulse-width-modulation of LED 72 is transferred within cable 50 as DC current, completely eliminating any interference that would be caused if pulse-width-modulated current were transferred in cable 50.

Furthermore, by placing only driver 80 in handle 44, and generating the DC current, used when the LED is not in a PWM state, in CCU 14, embodiments of the present invention reduce the size of the handle compared to endoscope systems that have the DC source and driver 80 in the handle.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
    an endoscope, comprising:
        a tube having a proximal end and a distal end configured for insertion into a body cavity;
        an image sensor, mounted at the distal end and configured to generate image signals of a region of the body cavity in response to illumination received therefrom;

a handle, configured to fixedly connect to the proximal end of the tube and configured to be held by an operator of the endoscope for manipulation thereof;

a driver circuit mounted within the handle, which is powered by a direct (DC) current and is configured to generate pulse-width-modulated (PWM) current; and an illumination source, mounted within the handle, configured to receive the PWM current and in response to illuminate the body cavity so as to provide the illumination received therefrom;

a camera control unit (CCU), which is external to the endoscope and is configured to provide the DC current to the driver circuit, to control the image sensor and to generate an image of the body cavity in response to receipt of the image signals, and to output a digital control signal indicative of a target luminous flux of the illumination source while varying a level of the DC current according to the target luminous flux; and a single cable connected between the CCU and the handle and configured to transfer the DC current and the digital control signal to the driver circuit and to transfer the image signals to the CCU, wherein the driver circuit is configured to generate and apply the PWM current to the illumination source when the digital control signal indicates that the target luminous flux is below a predefined bounding value, and to pass the DC current through to supply the DC current to the illumination source when the digital control signal indicates that the target luminous flux is above the predefined bounding value.

2. The apparatus according to claim 1, wherein the illumination source comprises a light emitting diode (LED).

3. The apparatus according to claim 2, wherein the PWM current is supplied by the driver circuit to the LED at a duty cycle, and wherein a current provided by the driver circuit in an on-state of the duty cycle comprises a minimum operating current of the LED.

4. A method comprising:

inserting a tube of an endoscope into a body cavity, the tube having a proximal end and a distal end;

mounting an image sensor of the endoscope at the distal end and generating with the image sensor image signals of a region of the body cavity in response to illumination received therefrom;

fixedly connecting a handle of the endoscope to the proximal end of the tube, the handle being configured to be held by an operator of the endoscope for manipulation thereof;

mounting a driver circuit within the handle, wherein the driver circuit is configured to generate a pulse-width-modulated (PWM) current;

powering the driver circuit by a direct (DC) current;

mounting an illumination source within the handle, and configuring the source to receive the PWM current and in response to illuminate the body cavity so as to provide the illumination received therefrom;

configuring a camera control unit (CCU), which is external to the endoscope, to provide the DC current to the driver circuit, to control the image sensor and to generate an image of the body cavity in response to receipt of the image signals;

outputting from the CCU a digital control signal indicative of a target luminous flux of the illumination source while varying a level of the DC current according to the target luminous flux;

connecting a single cable between the CCU and the handle and transferring the DC current and the digital control signal to the driver circuit and transferring the image signals to the CCU via the single cable;

generating and applying the PWM current from the driver circuit to the illumination source when the digital control signal indicates that the target luminous flux is below a predefined bounding value; and passing the DC current through to supply the DC current to the illumination source when the digital control signal indicates that the target luminous flux is above the predefined bounding value.

5. The method according to claim 4, wherein the illumination source comprises a light emitting diode (LED).

6. The method according to claim 5, wherein the PWM current is supplied by the driver circuit to the LED at a duty cycle, and wherein a current provided by the driver circuit in an on-state of the duty cycle comprises a minimum operating current of the LED.

\* \* \* \* \*